US 9,060,758 B2

(12) United States Patent
Dasbach et al.

(10) Patent No.: US 9,060,758 B2
(45) Date of Patent: Jun. 23, 2015

(54) NEEDLE ASSEMBLY STORAGE DEVICE

(75) Inventors: Uwe Dasbach, Frankfurt am Main (DE); Verena Hofmann, Frankfurt am Main (DE); Gunnar Jung, Mainz (DE); Peter Nober, Rommersheim (DE); Leo Zeimetz, Büttelborn (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 14/110,927

(22) PCT Filed: Apr. 11, 2012

(86) PCT No.: PCT/EP2012/056586
§ 371 (c)(1),
(2), (4) Date: Oct. 10, 2013

(87) PCT Pub. No.: WO2012/140087
PCT Pub. Date: Oct. 18, 2012

(65) Prior Publication Data
US 2014/0027329 A1  Jan. 30, 2014

(30) Foreign Application Priority Data

Apr. 13, 2011  (EP) ................................. 11162333

(51) Int. Cl.
| B65D 83/10 | (2006.01) |
| B65G 47/14 | (2006.01) |
| A61B 19/02 | (2006.01) |
| A61M 5/00 | (2006.01) |

(52) U.S. Cl.
CPC ............ *A61B 19/0262* (2013.01); *A61M 5/002* (2013.01); *A61M 2005/004* (2013.01)

(58) Field of Classification Search
CPC ............. A61B 19/0262; A61M 5/002; A61M 2005/004
USPC .................. 206/338–347, 366, 380–383, 533; 221/1, 2, 25, 70, 101, 103
See application file for complete search history.

(56) References Cited

U.S. PATENT DOCUMENTS

| 2,771,182 | A | * | 11/1956 | Messmer | ................ 206/382 |
| 3,297,198 | A | | 1/1967 | Wright, Jr | |
| 3,858,722 | A | * | 1/1975 | Haas | ................ 206/380 |
| 4,756,423 | A | * | 7/1988 | Holtsch | ................ 206/533 |
| 5,762,199 | A | * | 6/1998 | Aguilera | ................ 206/533 |
| 5,873,462 | A | | 2/1999 | Nguyen et al. | |
| 7,134,500 | B2 | | 11/2006 | Ramakrishnan et al. | |
| 2005/0269227 | A1 | | 12/2005 | Erickson et al. | |
| 2012/0037655 | A1 | * | 2/2012 | DiBiasi | ................ 221/1 |

FOREIGN PATENT DOCUMENTS

| WO | 2009128773 A1 | 10/2009 |
| WO | 2009136193 A1 | 11/2009 |

* cited by examiner

*Primary Examiner* — Bryon Gehman
(74) *Attorney, Agent, or Firm* — McDonnell Boehnen Hulbert & Berghoff LLP (57) ABSTRACT

Described is a needle assembly storage device comprising a housing having an opening adapted to receive an injection device, an array of needle assembly storage compartments moveably disposed within the housing, and an actuator adapted to cause movement of the array, wherein actuation of the actuator aligns a given needle assembly compartment with the opening.

21 Claims, 12 Drawing Sheets

NEEDLE ASSEMBLY STORAGE DEVICE

CROSS REFERENCE TO RELATED APPLICATIONS

The present application is a U.S. National Phase Application pursuant to 35 U.S.C. §371 of International Application No. PCT/EP2012/056586 filed Apr. 11, 2012, which claims priority to European Patent Application No. 11162333.6 filed Apr. 13, 2011. The entire disclosure contents of these applications are herewith incorporated by reference into the present application.

FIELD OF INVENTION

The invention relates to a device for storage of needle assemblies for use with, for example, injection devices.

BACKGROUND

Patients suffering from diseases like diabetes have to frequently self-administer injections. Injection devices like auto-injectors or pen injectors have been developed to facilitate self-administering injections. Typically, such injection devices are re-usable and refitted with sterile injection needle assemblies to minimize the risk of infections. However, such needle assemblies generally come packaged in a box, which is inconvenient for the patient to transport. To solve this problem, needle assembly storage devices were developed. A conventional needle assembly storage device contains a plurality of injection needle assemblies arranged in a portable container. Such conventional needle assembly storage devices are discussed in U.S. Pat. No. 7,134,550 and WO 2009/136193.

However, there remains a need for needle assembly storage devices which provide for portability of needle assemblies in a convenient manner and allow for disposing of used needle assemblies.

SUMMARY

It is an object of the present invention to provide improved means for storing and disposing needle assemblies.

In an exemplary embodiment, a needle assembly storage device according to the present invention comprises a housing having an opening adapted to receive an injection device, an array of needle assembly storage compartments moveably disposed within the housing, and an actuator adapted to cause movement of the array, wherein actuation of the actuator aligns a given needle assembly compartment with the opening. Consecutive needle assembly storage compartments may be coupled via a hinge. A needle assembly storage compartment comprises a storage cavity having a first portion housing a needle hub and a second portion housing an injection needle coupled to the needle hub, and an opening. The second portion may have a cross-sectional shape of one of a circle and a triangle. The array may be shaped as one of a ring, an ellipsoid, and a helix. The openings of the needle assembly storage compartments may be sealed by at least one membrane.

The housing may comprise a top wall, a bottom wall, and a side wall coupling the top wall to the bottom wall. A hinge may connect one of the top wall and the bottom wall to the side wall, and a connector may selectively lock the one of the top wall and the bottom wall to the side wall.

The actuator may include a geared surface mating with a corresponding geared surface on the array. The actuation of the actuator may move the array a predetermined step distance, which may be substantially equal to a width of one of the needle assembly storage compartments.

In an exemplary embodiment, the needle assembly storage device may comprise a lock for preventing the actuator from being actuated after a number of actuations equals a number of the needle assembly storage compartments in the array. An indicator may be disposed on the housing and display a number of unused needle assemblies in the array.

A door may be disposed on the housing and adapted to selectively cover the opening. The door can be movable from a closed position covering the opening to an open position in which the door is uncovered, and the door may be biased in the closed position. A locking mechanism in the exemplary embodiment of the needle assembly storage device may prevent movement of at least one of the actuator and the array. In one exemplary embodiment, the locking mechanism comprises a notch formed on the actuator, and a protrusion formed on the door, such that when the door is in the closed position, the protrusion engages the notch and prevents actuation of the actuator. In another exemplary embodiment, the locking mechanism comprises at least one recess formed on the array, and a latch arm disposed in the housing and moveable between a first position engaging the recess and a second position disengaging the recess. When the latch arm is in the first position, movement of the array in one direction is prevented. In another exemplary embodiment, the locking mechanism comprises a cog wheel including a plurality of cogs and at least one projection formed on the actuator. When the actuator moves in a first direction, the at least one projection is deflected by the cogs and when the at least one projection abuts one of the plurality of cogs, movement of the actuator in a second direction is prevented.

The actuator may be one of a dial wheel, a lever, a switch, and a button. A guide may be formed around the opening to align the injection device with a needle assembly in a given one of the needle assembly storage compartments. The array may be formed in a linear arrangement by injection-molding, filled with needle assemblies and subsequently formed into a ring shape.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
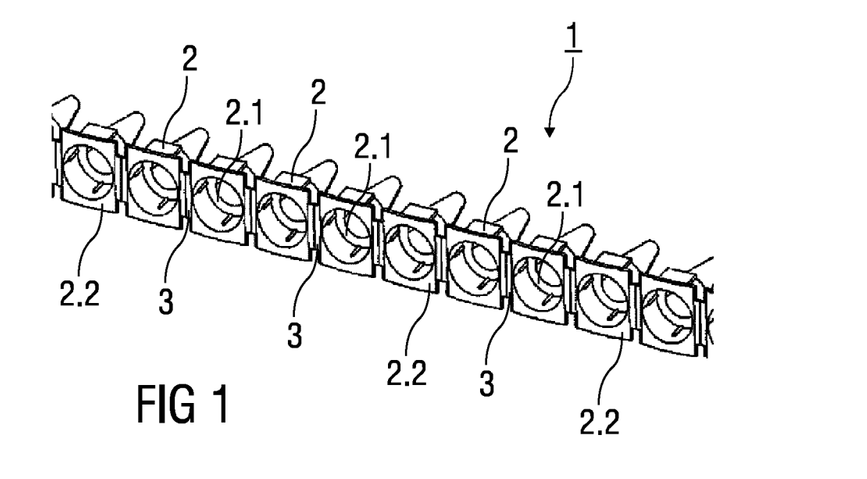
FIG. 1 shows an isometric view of a linear array of interconnected needle storage compartments according to an exemplary embodiment of the present invention.

FIG. 1 shows an exemplary embodiment of an array 1 of needle assembly storage compartments 2. In the exemplary embodiment, the array 1 may be linear and consecutive storage compartments 2 may be connected by a hinge 3. In the exemplary embodiment, the hinge 3 connects the storage compartments 2 near their openings; however, those of skill in the art will understand that the hinge 3 may be formed between any portions of the consecutive storage compartments 2. The hinge 3 may allow relative motion between the consecutive storage compartments 2 in one or more planes. For example, a first storage compartment may rotate relative to a second, consecutive storage compartment about the hinge 3. The array 1 (and/or portions thereof) may be manufactured by injection moulding and made of, for example, a flexible plastic material capable of resisting high strain. For example, semi-crystalline materials plastic materials like polyamide, polyoxymethylene, polybutylene terephthalate, polyethylene or polypropylene may be used. Alternatively, a thermoplastic elastomer may be used. Further, polyethylene or polypropylene may be used.

In an exemplary embodiment, the array 1 may be manufactured from at least two different materials, e.g., by a two-shot injection moulding. For example, the needle assembly storage compartments 2 may be made from a relatively stiff plastic material, whereas the hinges 3 may be made from a more flexible material, e.g., semi-crystalline plastic. Alternatively, the array 1 may be manufactured from rubber or silicon and the needle assembly storage compartments 2 may be manufactured from a plastic.

In an exemplary embodiment, the needle assembly storage compartment 2 may include a storage cavity 2.1 adapted to retain an injection needle 6 mounted to a needle hub 7 and an opening 2.2 providing access to the storage cavity 2.1. In an exemplary embodiment, the storage compartment 2 may include a first cylindrical portion sized and shaped to correspond to the needle hub 7, a frusto-conical portion distal of the cylindrical portion, and a second cylindrical portion 2.3 distal of the frusto-conical portion sized and shaped to correspond to the needle 6. The openings 2.2 of the needle assembly storage compartments 2 in the array 1 may face in a single direction (as shown in the exemplary embodiment in FIG. 1) so as to allow access to the storage cavities from one side, or may face in alternate directions.

Figure 2:
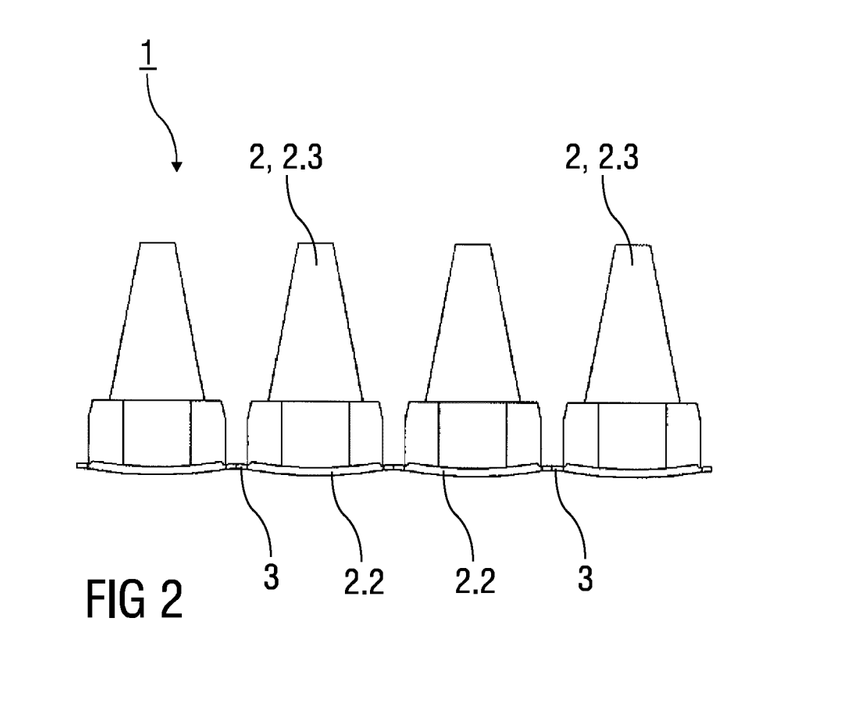
FIG. 2 shows a top view of a section of the linear array of needle assembly storage compartments according to an exemplary embodiment of the present invention.

FIG. 2 shows an exemplary embodiment of the needle assembly storage compartments 2 according to the present invention. In this exemplary embodiment, the openings 2.2 of the needle assembly storage compartments 2 are aligned in a plane. However, as shown in an exemplary embodiment depicted in FIG. 3, the array 1 may be formed into a ring in which the openings 2.2 face radially outward. In this exemplary embodiment, a circumference of a curvature L of the ring may be determined by a number of the needle assembly storage compartments 2, a size (e.g., width and/or depth) of the needle assembly storage compartments 2, orientation of consecutive needle assembly storage compartments 2, and/or a degree of flexibility of the hinges 3. Different configurations (e.g., ring, ellipsoid, helix, etc.) of the array 1 may be utilized with different housings, containers and/or dispensers, as explained further below.

Figure 3:
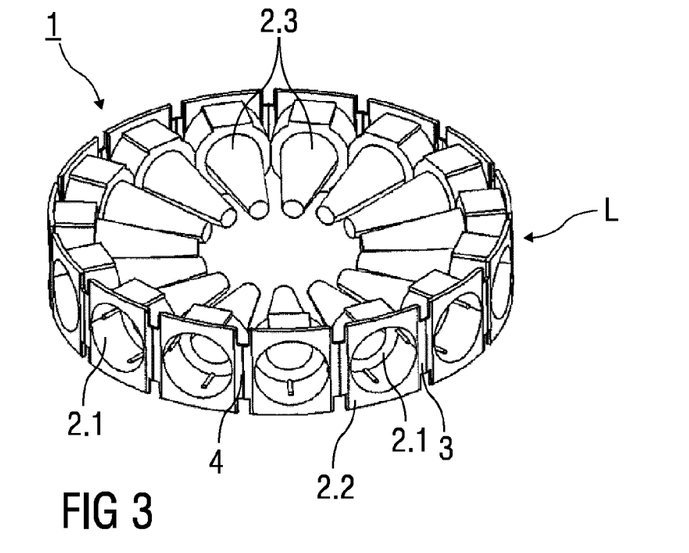
FIG. 3 shows an isometric view of a circular array of interconnected needle assembly storage compartments according to an exemplary embodiment of the present invention.

The array 1 may be formed into a ring by, for example, interconnecting terminal ends of the needle assembly storage compartments 2 located at respective ends of the array 1. The terminal ends may be adhered together (chemically or mechanically) or welded together. For example, a connector 4 may be used to mechanically clip the terminal ends together.

Figure 4:
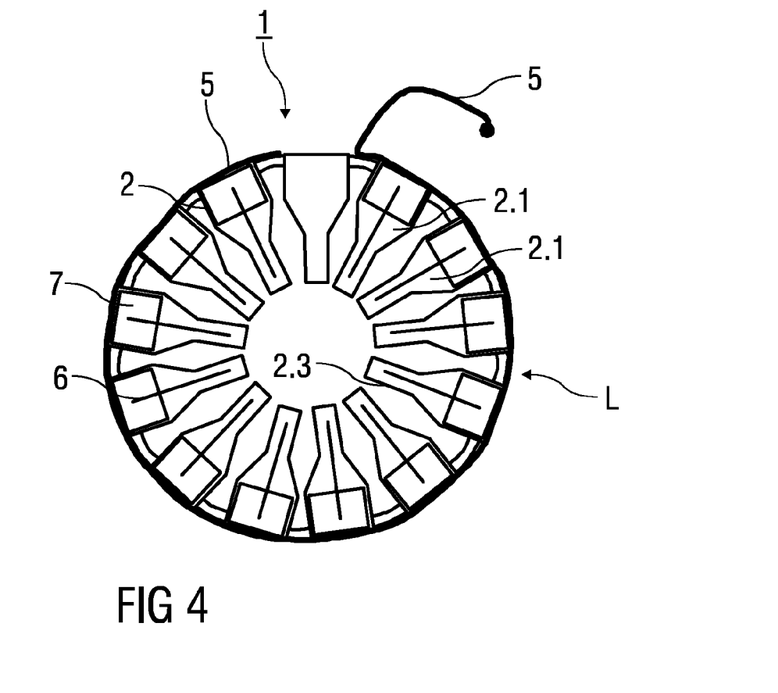
FIG. 4 shows a sectional view of the circular array of needle assembly storage compartments according to an exemplary embodiment of the present invention.

As shown in the exemplary embodiment in FIG. 4, the openings 2.2 of the needle assembly storage compartments 2 may be sealed by a removable membrane 5. In an exemplary embodiment, the membrane 5 may be a film which covers each respective one of the openings 2.2. In another exemplary embodiment, the membrane 5 may be a continuous film that covers all of the openings 2.2. The membrane 5 provides a sterile seal for unused needle assemblies in the needle assembly storage compartments 2.

Figure 5A:
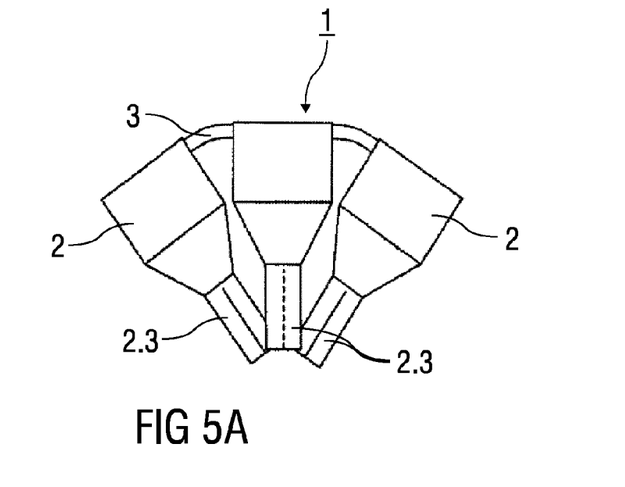
FIGS. 5A and 5B show a section of interconnected needle assembly storage compartments according to an exemplary embodiment of the present invention.
Figure 5B:
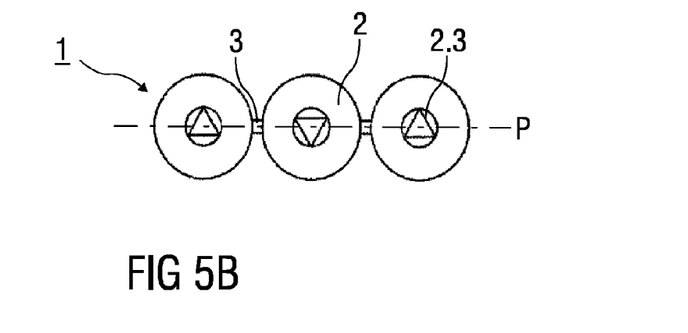

FIGS. 5A and 5B show another exemplary embodiment of the needle assembly storage compartment 2 having a second cylindrical portion 2.3 with a different geometry. In this exemplary embodiment, the second portion 2.3 may have a triangular cross-section (shown in FIG. 5B). Use of the triangular cross-section enables space savings relative to a cylindrical second portion 2.3. For example, when the array 1 is formed into a ring (or other shape having an arc), the second portions 2.3 of consecutive needle assembly storage compartments 2 have an alternating orientation. Thus, whereas consecutive cylindrical second portions 2.3 may only have a single point of contact (e.g., one point of each circumference), consecutive triangular second portions 2.3 may have a full surface (triangle leg) of contact. In this exemplary embodiment, a radius of the curvature L of the array 1 may be less than the radius of curvature L of the array 1 in which the second portions 2.3 of the needle assembly storage compartments 2 are cylindrical.

Figure 6:
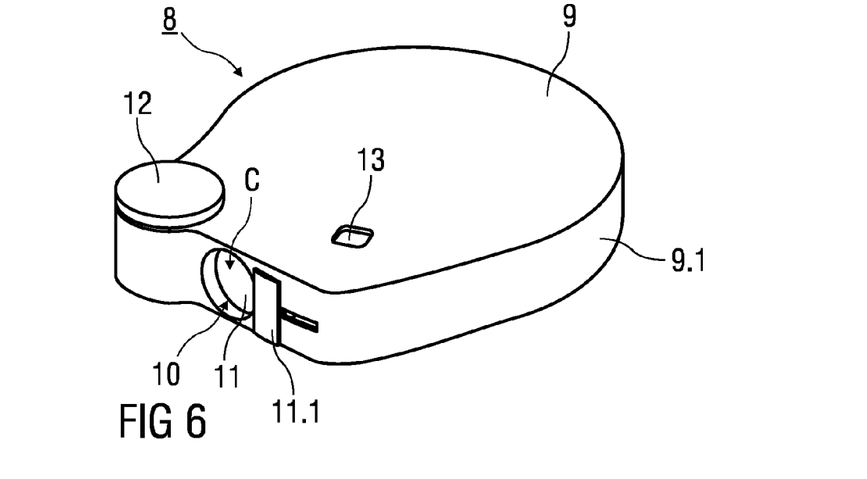
FIG. 6 shows a needle assembly storage device in an isometric view according to an exemplary embodiment of the present invention.

FIG. 6 shows an isometric view of an exemplary embodiment of a needle assembly storage device 8 for housing the array 1 of the needle assembly storage compartments 2. The storage device 8 provides a portable, sterile receptacle for the needle assemblies. The storage device 8 may be any size and/or shape. In an exemplary embodiment, the storage device 8 is substantially circular and has a diameter of about 3-6 inches and a width substantially equal to a width of the array 1.

Figure 7:
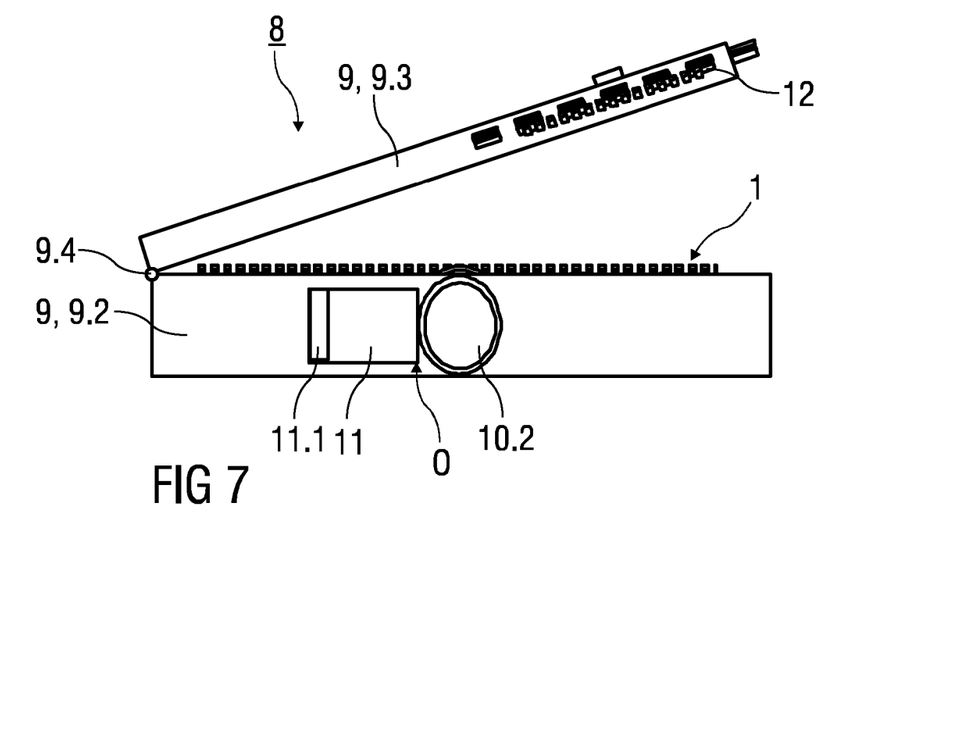
FIG. 7 shows a side view of the needle assembly storage device of FIG. 6 with an opened cover.
Figure 8:
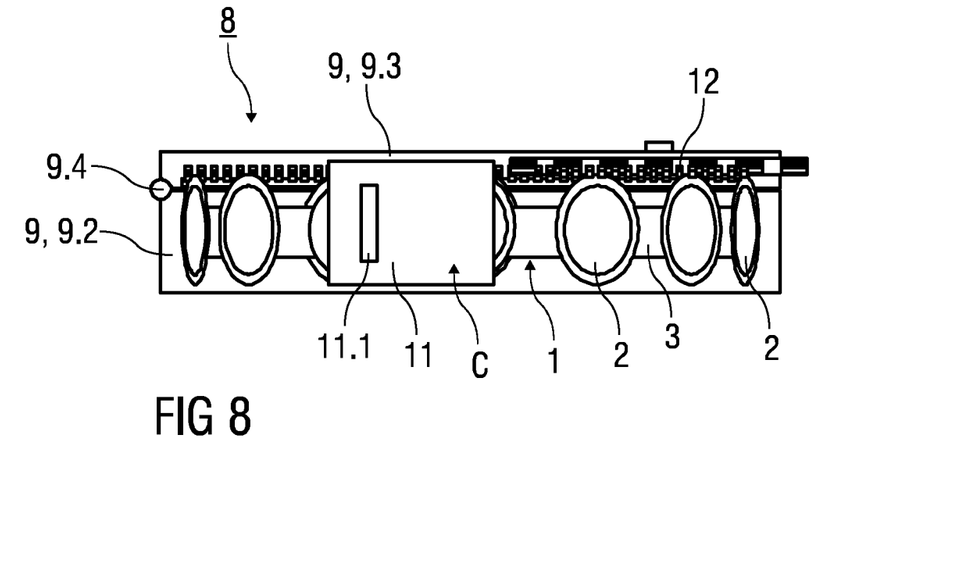
FIG. 8 shows a side view of the needle assembly storage device of FIG. 6 with the cover closed.

In an exemplary embodiment, the needle assembly storage device 8 comprises a housing having a top wall 9 and a bottom wall connected at their respective edges by a side wall 9.1. The top wall 9, bottom wall and side wall 9.1 may be integrally formed and/or sealed (e.g., mechanically, chemically, welded) if the storage device 8 is intended as a disposable device. In an exemplary embodiment in which the storage device 8 may be reused, at least one of the top and bottom walls may be coupled to the side wall 9.1 via a hinge and/or connector which allows the user to open the storage device 8, e.g., for replacing an array 1 of used needle assemblies with an array 1 of unused needle assemblies. For example, as shown in the exemplary embodiment in FIG. 7, the side wall 9.1 may be integrally formed with the bottom wall to form a base member 9.2, and the top wall 9 may be a cover 9.3 attached thereto via a hinge 9.4. The cover 9.3 can be opened so that the array 1 may be replaced. Preferably, a locking mechanism allows the cover 9.3 to be locked in a closed position.

An opening 10 is formed into the side wall 9.1 which provides access to the needle assembly storage compartments 2 of the array 1. In an exemplary embodiment, a diameter of the opening 10 is substantially equal to a diameter of the needle hub 7 of a needle assembly. The opening 10 may be selectively covered by a door 11 arranged on the storage device 8. In the exemplary embodiment shown in FIG. 6, the door 11 is mounted on the side wall 9.1 and selectively slides between a first position covering the opening 10 (e.g., a closed position C) and a second position where the opening 10 is uncovered (e.g., an open position O). To facilitate the movement of the door 11 between the first and second positions, the door 11 may include a handle 11.1 and/or a textured surface. In an exemplary embodiment, the door 11 may be positioned manually in the first and second positions. In another exemplary embodiment, the door 11 may be biased in the first position (e.g., the closed position C) by a spring.

Figure 9:
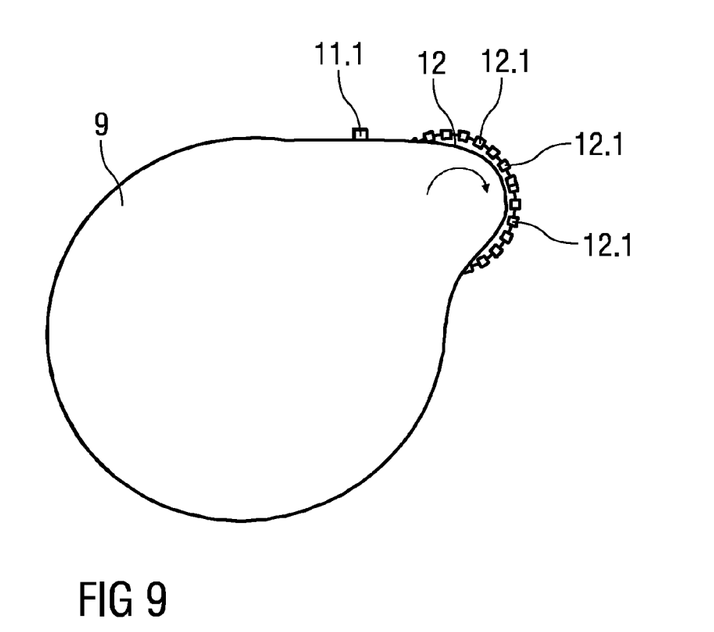
FIG. 9 shows the needle assembly storage device of FIG. 6 in a top view.

In an exemplary embodiment, the needle assembly storage device 8 comprises an actuator 12 that is adapted to be manually actuated to move the array 1 within the storage device 8. In an exemplary embodiment, the actuator 12 is a dial wheel which engages the array 1 such that rotation of the actuator 12 causes movement of the array 1. For example, the array 1 may include a toothed edge or surface and the actuator 12 may include a gear or geared surface which mates with the edge/surface of the array 1. Those of skill in the art will understand that the actuator 12 may be a switch, a button, a lever, etc. As shown in FIG. 9, the actuator 12 may include a gripping surface (e.g., a handle, rubber and/or plastic cover, a textured surface, etc.) to facilitate actuation by the user and prevent accidental actuation.

In an exemplary embodiment, movement of the actuator 12 may be limited, on a per-actuation basis, to a predefined range of motion, e.g., a step distance SD. For example, in an exemplary embodiment in which the actuator 12 is a dial wheel, the dial wheel may be limited to a predetermined range of angular rotation such that rotation of the dial wheel will be sufficient to move the array 1 a defined step distance SD to align the opening 2.2 of the next consecutive needle assembly storage compartment 2 with the opening 10. Thus, one actuation of the actuator 12 may advance the array 1 by the step distance which may be substantially equal to a width of one of the needle assembly storage compartments 2. In another exemplary embodiment, the actuator 12 (and/or the array 1) may be limited to movement in one predefined direction, e.g., so that the user cannot attempt to reuse used needle assemblies.

The actuator 12 may further comprise a locking mechanism which prevents actuation after a number of actuations equals the number of needle assemblies in the array 1. For example, a brake or lock may be triggered after a last actuation which prevents further actuation of the actuator 12.

In an exemplary embodiment, the needle assembly storage device 8 comprises an indicator 13 capable of indicating a number of unused needle assemblies remaining in the array 1. In one exemplary embodiment, the indicator 13 may comprise a numbered dial which is advanced (e.g., decremented) for each actuation of the actuator 12 and contains numbers equal to the number of needle assemblies in the storage device 8. The indicator 13 may also include a symbol (e.g., a color, an "X", alpha-numeric) which indicates that all of the needle assemblies have been used. In another exemplary embodiment, the needle assembly storage compartments 2 of the array 1 may include numbered labels that are visible through a window formed on the storage device 8.

Figure 10:
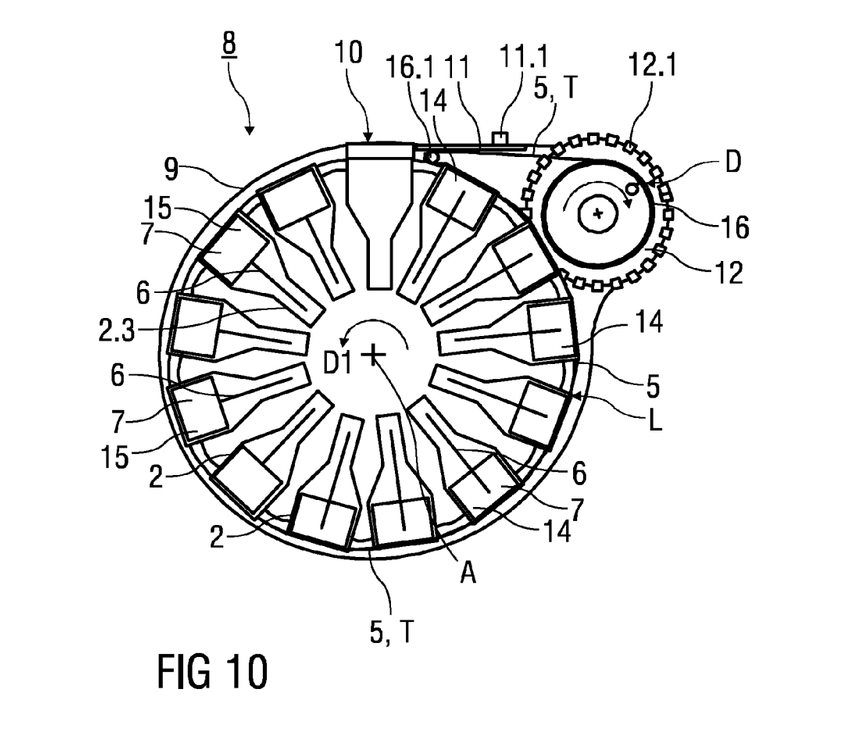
FIG. 10 shows the needle assembly storage device of FIG. 6 in a sectional view.

FIG. 10 shows a sectional view of an exemplary embodiment of the needle assembly storage device 8. In this exemplary embodiment, the array 1 is formed in a ring and rotatably disposed on an axis A. A portion of the array 1 engages a portion of the actuator 12 so that rotation of the actuator 12 causes rotation of the array 1 about the axis A. Prior to a first use, the door 11 may be covering the opening 10 and the opening 2.2 of the needle assembly storage compartment 2 aligned with the opening 10. The openings 2.2 of the remainder of the needle assembly storage compartments 2 may be covered by the membrane 5 (e.g., a continuous tape T). Alternatively, the opening 2.2 of the needle assembly storage compartment aligned with the opening 10 may be covered by the membrane 5, and sliding the door 11 to uncover the opening 10 may remove the membrane 5 from the opening 2.2.

The opening 10 may be sized and shaped to receive a distal end of an injection device. In an exemplary embodiment, a rim of the opening 10 may be sloped toward the opening 2.2 such that the injection device is directed to align with the opening 2.2 prior to insertion of the injection device into the needle hub 7 in the needle assembly storage compartment 2. Orienting the injection device relative to the needle assembly prior to engagement may prevent misaligned engagement (e.g., a mismatched threaded assembly). The needle hub 7 may include a coupling mechanism (e.g., threads, bayonet fittings, a frictional surface, snap-fits) for coupling to a corresponding coupling mechanism on the injection device.

In an exemplary embodiment, upon a first use, the door 11 is moved from the closed position C to the open position O, providing access to an unused needle assembly 14. The injection device is inserted into the opening 10 and coupled to the needle hub 7 of the unused needle assembly 14. The needle assembly is removed from the needle assembly storage compartment 2 and the door 11 is returned to the closed position C. After use, the used needle assembly 15 may be returned to the same needle assembly storage compartment 2.

For a subsequent use, the actuator 12 is actuated and the array 1 is rotated so that the opening 2.2 of a subsequent needle assembly storage compartment 2 is aligned with the opening 10. As the array 1 is rotated, the membrane 5 covering the opening 2.2 of the subsequent needle assembly storage compartment 2 may be removed. In an exemplary embodiment, a first end of the membrane 5 may be coupled to an inner cylinder 16 that is rotated based on movement of the actuator 12. Thus, as the actuator 12 is moved, the inner cylinder 16 rotates, separating the membrane 5 from the needle assembly storage compartment 2 and winding the membrane 5 around the inner cylinder 16. Separation of the membrane 5 may be accomplished by a guide roller 16.1. The guide roller 16.1 may be disposed within the storage device 8 substantially adjacent to the opening 10, and the membrane 5 may be wound around the guide roller 16.1 to the inner cylinder 16. Thus, as the needle assembly storage compartment 2 passes the guide roller 16.1, the rotation of the array 1 and the rotation of the inner cylinder 16 in opposite directions separate the membrane 5 from the opening 2.2 of the needle assembly storage compartment 2.

As understood by those of skill in the art, the winding of the membrane 5 around the inner cylinder 16 may facilitate movement of the array 1, such that less force is required to actuate the actuator 12.

Figure 11:
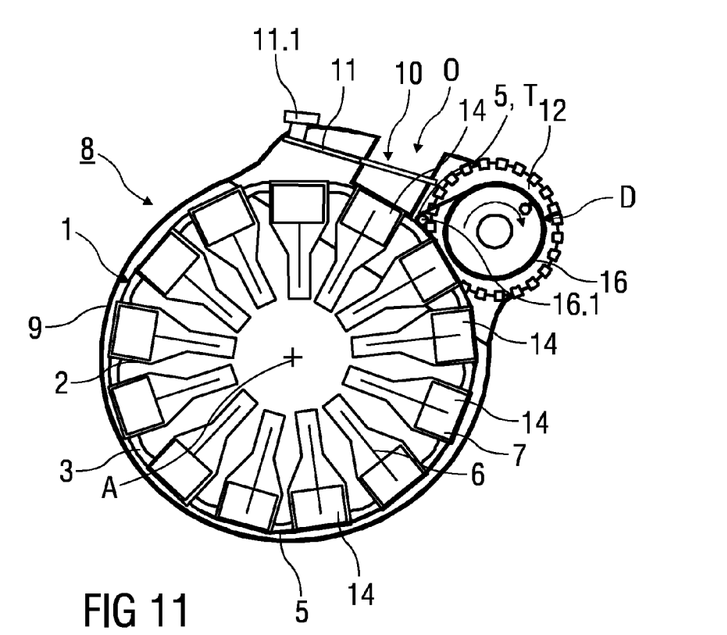
FIG. 11 shows a needle assembly storage device in a sectional view according to an exemplary embodiment of the present invention
Figure 12:
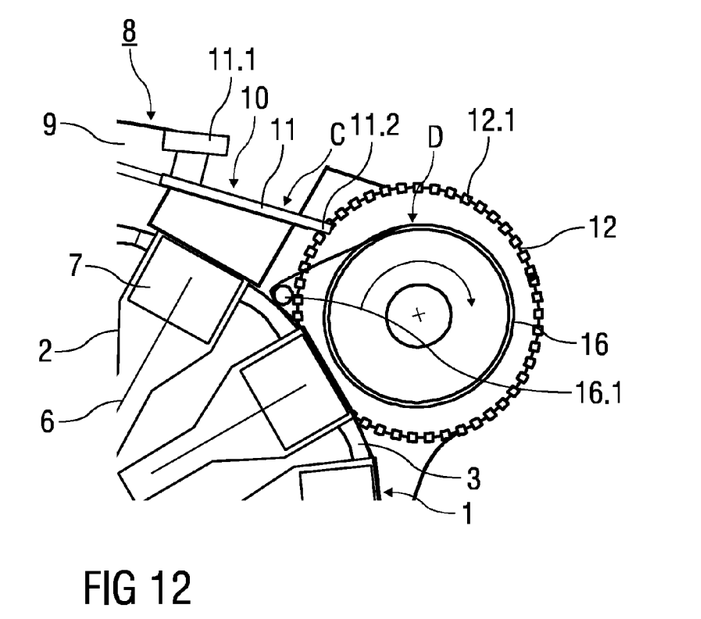
FIG. 12 shows details of a locking mechanism in a sectional view according to an exemplary embodiment of the present invention.

FIG. 11 shows another exemplary embodiment of the needle assembly storage device 8 according to the present invention. In this exemplary embodiment, a guide is formed around the opening 10 to guide the injection device into the needle storage compartment 2. The guide may be sized and shaped to receive a distal portion of the injection device. For example, the guide may be cylindrical and have a predetermined depth (e.g., about 0.25-1.0 inches).

FIGS. 12 to 16 show another exemplary embodiment of the needle assembly storage device 8 including a locking mechanism according to the present invention. In the exemplary embodiment shown in FIG. 12, the door 11 includes a protrusion 11.2 which, when the door 11 is in the closed position C, engages the actuator 12 and prevents the actuator 12 from movement. For example, at least one notch 12.1 may be arranged on the actuator 12, and the protrusion 11.2 may fit within the notch 12.1 when the door 11 is in the closed position C and prevent movement of the actuator 12. Those of skill in the art will understand that the first locking mechanism L1 (e.g., the protrusion 11.2 and the notch 12.1) may be embodied in varying structures and may or may not directly engage the actuator 12. For example, the first locking mechanism L1 may, when activated, temporarily separate the actuator 12 from the array 1 or cover the actuator 12.

Figure 13:
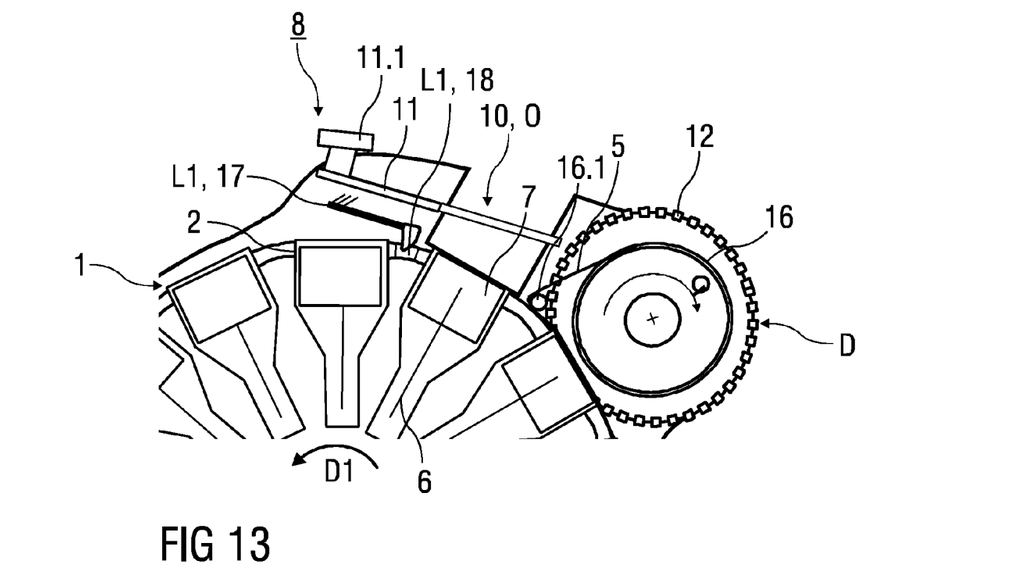
FIG. 13 shows details of a first locking means according to an exemplary embodiment of the present invention
Figure 14A:
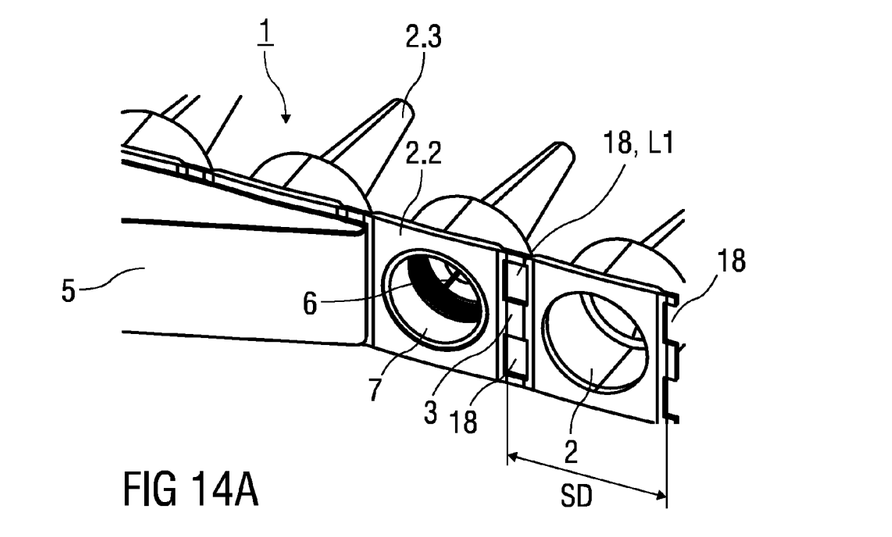
FIGS. 14A and 14B show details of the array of needle assembly storage compartments according to an exemplary embodiment of the present invention

FIG. 13 shows another exemplary embodiment of a locking mechanism L1 according to the present invention. In this exemplary embodiment, the locking mechanism L1 includes a latch arm 17 disposed within the storage device 8 and at least one recess 18 formed on the array 1 of the needle assembly storage compartments 2, illustrated in more detail in FIGS. 14A and 14B. As shown in FIG. 14A, the recess 18 may be formed in the hinge 3 of the array 1. In another exemplary embodiment, the recess 18 may be formed along a lateral edge of the array 1. Those of skill in the art will understand that there may be any number of recesses formed on the array 1. Preferably, consecutive recesses 18 are separated by a distance approximately equal to the width of a needle assembly storage compartment 2.

Figure 14B:
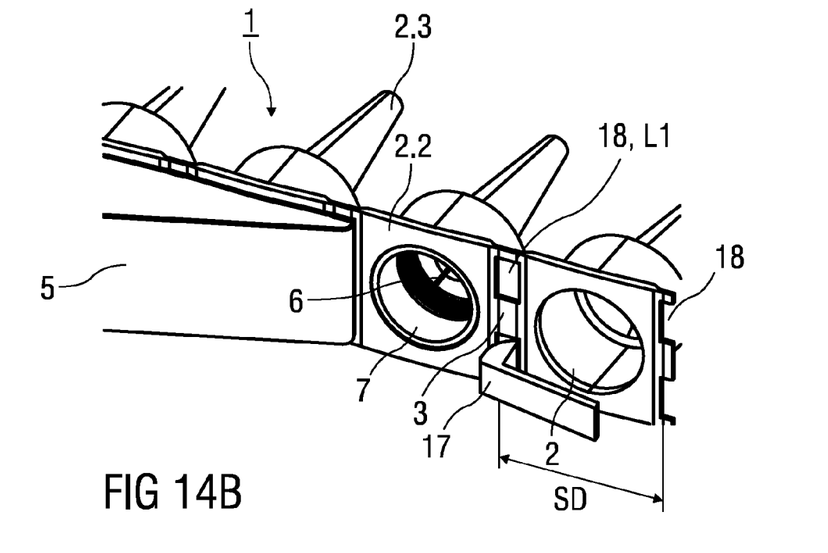

As shown in FIG. 14B, the latch arm 17 may be elastic and biased in a first position in the recess 18. When the latch arm 17 is in the recess 18, movement of the array 1 in a reverse direction (the direction opposite the direction of movement caused by the actuator 12) is prevented. However, movement of the array 1 in the direction caused by the actuator 12 is enabled, because movement of the array 1 in that direction causes the latch arm 17 into a second position, disengaged from the recess 18, allowing free movement of the array 1 until the latch arm 17 encounters a subsequent recess 18. The latch arm 17 may prevent a user from gaining access to and using previously used needle assemblies.

Figure 15:
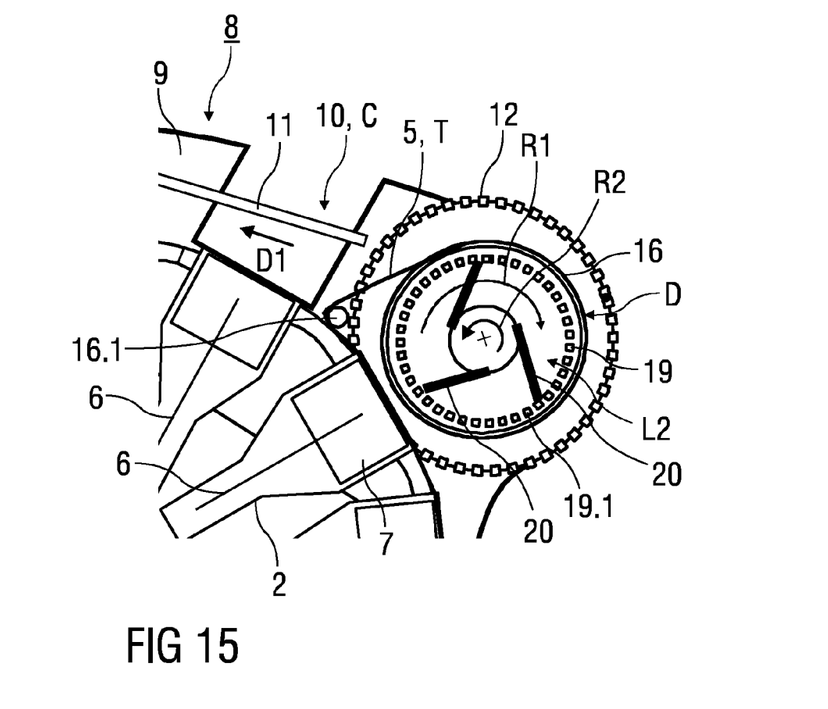
FIG. 15 shows details of a second locking means according to an exemplary embodiment of the present invention.

FIG. 15 shows an exemplary embodiment of a locking mechanism L2 according to the present invention. In this exemplary embodiment, the locking mechanism L2 is utilized to limit movement of the actuator 12 to a predetermined direction. For example, when the actuator 12 is arranged as the dial wheel, the locking mechanism L2 ensures that the dial wheel only rotates in one rotational direction, e.g., to advance the array 1 within the housing 9 in the first direction D1.

In an exemplary embodiment, the locking mechanism L2 comprises a cog wheel 19 disposed within the inner cylinder 16 that jointly rotates therewith when the actuator 12 is moved. The cog wheel 19 includes a plurality of cogs 19.1 adapted to be engaged by at least one projection 20 disposed on an axis of the dial wheel or the inner cylinder 16. The projection 20 is resiliently deflected when the dial wheel (or the inner cylinder 16) rotates in a first rotational direction R1 so as to disengage from the cog 19.1 allowing for advancement of the array 1 in the first direction. However, when a force is exerted upon dial wheel (or the inner cylinder 16) in a second rotational direction R2 opposite to the first rotational direction R1, the projection 20 abuts the cog 19.1, preventing rotation in the second rotational direction R2.

Figure 16:
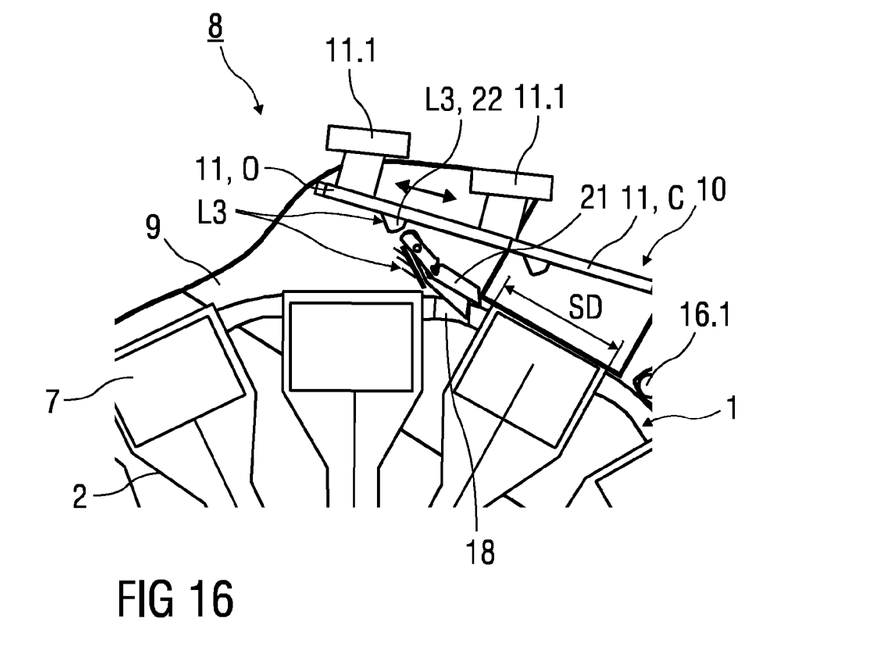
FIG. 16 shows details of a third locking means according to an exemplary embodiment of the present invention.

FIG. 16 shows an exemplary embodiment of a locking mechanism L3 according to the present invention. A latch arm 21 may be hingedly disposed in the storage device 8 and biased in a position to engage the array 1 (and/or the recess 18). When the door 11 is in the closed position C, the latch arm 21 may be in contact with a surface of the array 1 but may not prevent movement of the array 1. For example, the latch arm 21 may maintain contact with the array 1 as the array 1 is moved, until the latch arm 21 encounters the recess 18. When the door 11 is in the open position O, the latch arm 21 may be disposed in the recess 18, and movement of the latch arm 21 may be prevented by a projection 22 formed on an interior side of the door 11. For example, movement of the array 1 may cause the latch arm 21 to rotate about the hinge, but the rotation may be limited when the latch arm 21 abuts the projection. Because the latch arm 21 may not disengage the recess 18, the latch arm 21 may prevent movement of the array 1.

Those of skill in the art will understand that the locking mechanisms may be utilized alone or in any combination.

Figure 17:
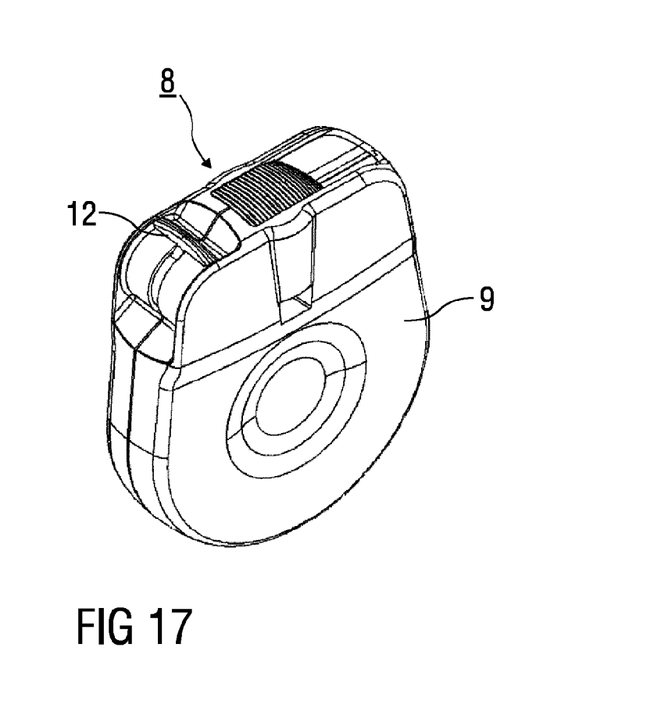
FIG. 17 shows an isometric view of a needle assembly storage device according to an exemplary embodiment of the present invention.

FIG. 17 shows an exemplary embodiment of the needle assembly storage device 8 in which the actuator 12 is a lever. The lever may be spring loaded such that it pivots about an angle of approximately 90 degrees upon manual actuation to move the array 1 within the storage device 8. After manual actuation, the lever may be returned to its original position by a spring (e.g., a torsion spring).

Figure 18:
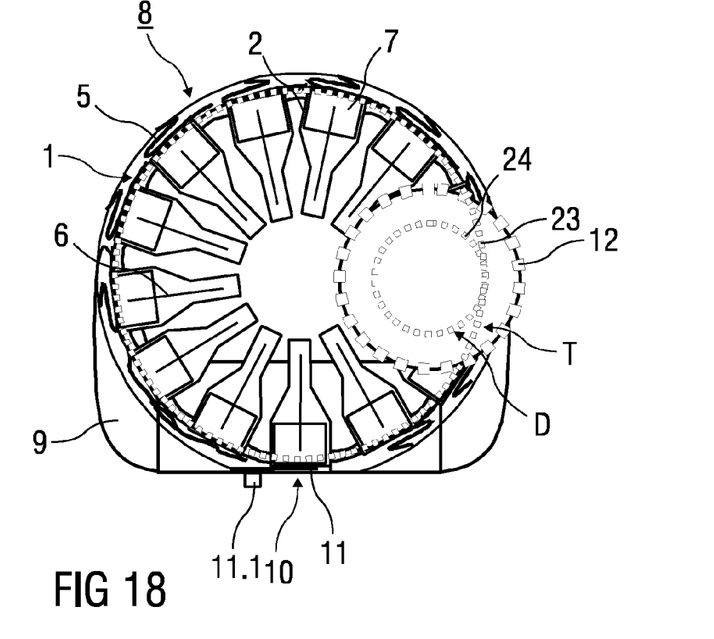
FIG. 18 shows a needle assembly storage device in a sectional view according to an exemplary embodiment of the present invention.

FIG. 18 shows another exemplary embodiment of the needle assembly storage device 8 according to the present invention. In this exemplary embodiment, the actuator 12 is a dial wheel which includes an axial member having a gear wheel 24 (or a toothed surface) which mates with a plurality of cogs 23 on the array 1. Thus, rotation of the dial wheel causes the gear wheel 24 to move the array 1 within the storage device.

Figure 19:
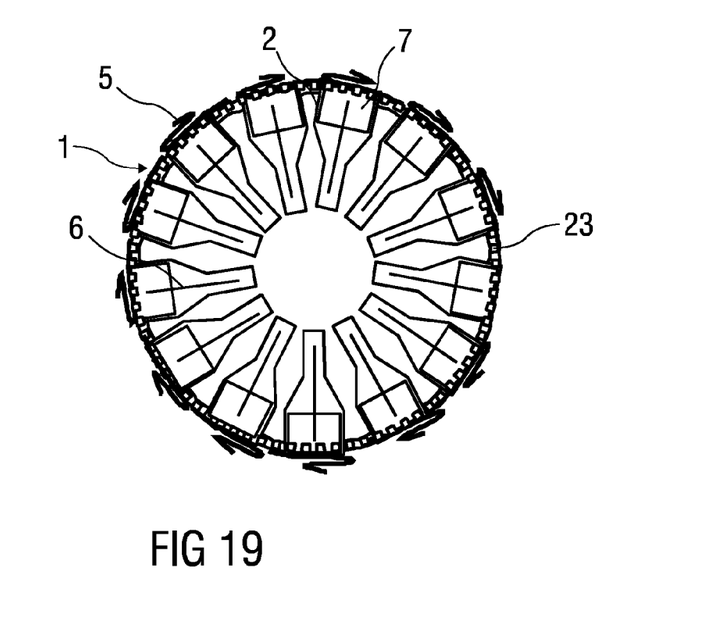
FIG. 19 shows a circular array of needle assembly storage compartments according to an exemplary embodiment of the present invention.

FIG. 19 shows an exemplary embodiment of the array 1 in which the membrane 5 is a separate film disposed on each of the openings 2.2 of the needle assembly storage compartments 2. In this exemplary embodiment, the separate films may be manually removed when a given needle assembly storage compartment 2 is aligned with the opening 10. In another exemplary embodiment, the projection 20 formed on the interior side of the door 11 may be used to remove the film from the opening 2.2 when the door 11 is moved from the closed position C to the open position O. In another exemplary embodiment, a ridge formed on an interior of the storage device 8 adjacent the opening 10 may be used to remove the film. For example, as the needle assembly storage compartment 2 passes the ridge, a portion of the film may be engaged by the ridge and further movement of the array 1 may result in the film being separated from the opening 2.2.

Figure 20:
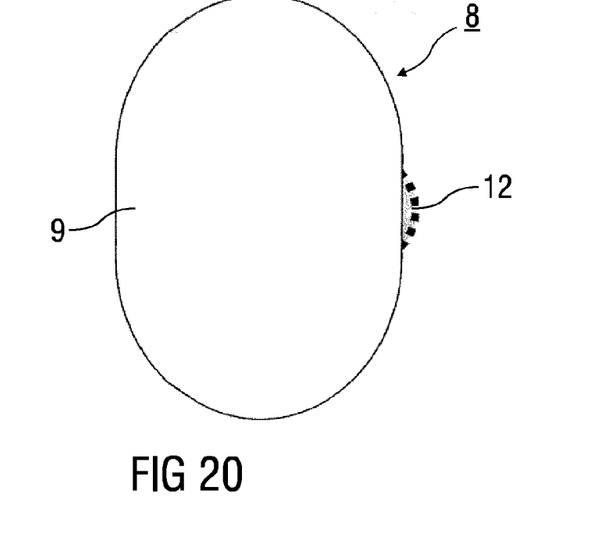
FIG. 20 shows a top view of a needle assembly storage device according to an exemplary embodiment of the present invention.
Figure 21:
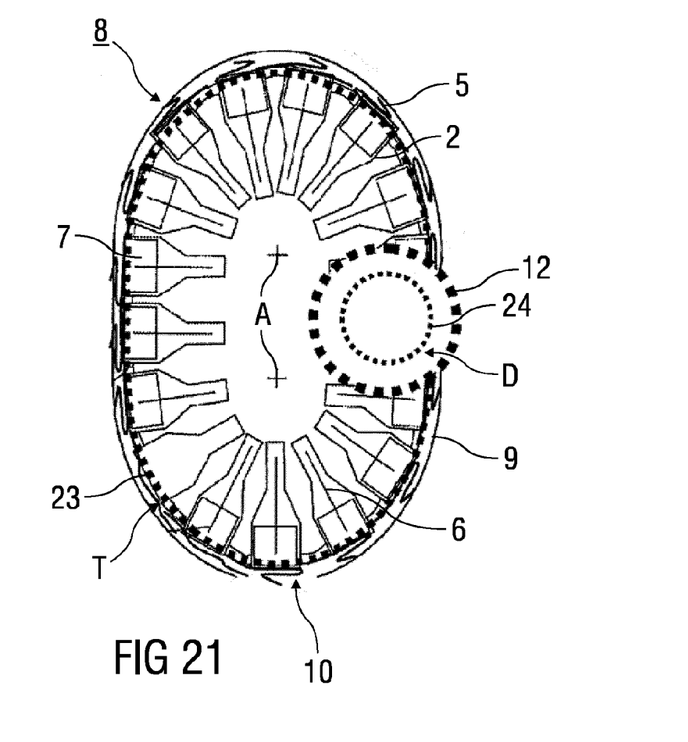
FIG. 21 shows the exemplary embodiment of the needle assembly storage device of FIG. 21 in a sectional view.

FIGS. 20 and 21 show an exemplary embodiment of the needle assembly storage device 8 in which the storage device 8 has a substantially elliptic cross-section.

Figure 22:
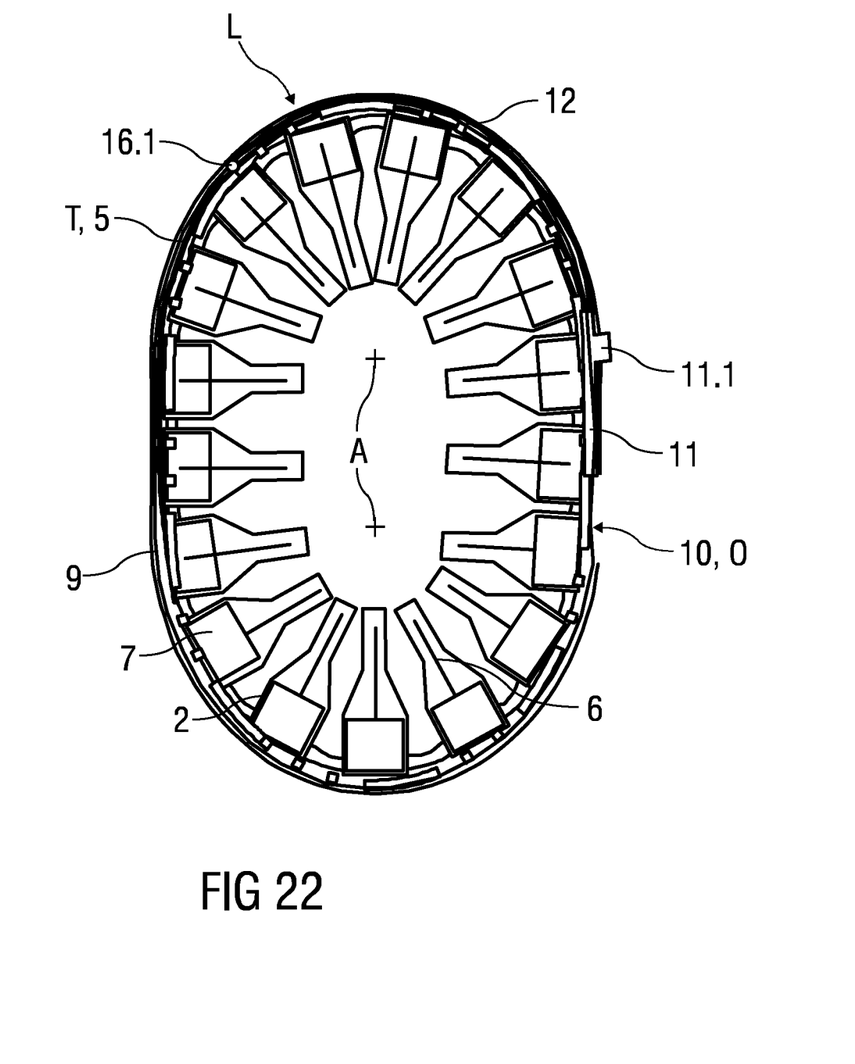
FIG. 22 shows a needle assembly storage device according to an exemplary embodiment of the present invention.

FIG. 22 shows another exemplary embodiment of the needle assembly storage device 8 according to the present invention. In this embodiment, the array 1 may be statically disposed in the storage device 8 and a wall of the storage device 8 may be moved relative to the array 1 to allow access to the needle assembly storage compartments 2. For example, the openings 2.2 of the needle assembly storage compartments 2 may be covered by the membrane 5. A first terminal end of the membrane 5 may be coupled to the wall, and a second terminal end of the membrane 5 may be coupled to a last one of the needle assembly storage compartments 2 in the array 1. The membrane 5 may be wrapped 180° around a guide roller 16.1 with the first terminal end trailing the second terminal end. Thus, when the wall is moved relative to the array 1, a distance between the first terminal end and the second terminal end of the membrane 5 decreases and the membrane 5 is separated from the opening 2.2 of the needle assembly storage compartments 2. In an exemplary embodiment, after the wall is moved a distance substantially equal to a width of a needle assembly storage compartment 2, the door 11 may be opened and the injection device may be inserted into the opening 10 to engage or remove a needle assembly. In another exemplary embodiment, the door 11 may not be used to cover the opening 10, but the sterility of the needle assemblies may be maintained by the membrane 5.

Those of skill in the art will understand that a ring, rollers, bearings, lubricant, etc. may be utilized to reduce any friction resulting from moving the wall over the membrane 5 which may remove (partially) the membrane 5 from the unused needle assembly storage compartments 2.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A needle assembly storage device comprising:
   a housing having an opening adapted to receive an injection device;
   an array of needle assembly storage compartments moveably disposed within the housing;
   an actuator adapted to cause movement of the array,
   wherein actuation of the actuator aligns a needle assembly compartment with the opening;
   wherein two adjacent needle assembly storage compartments within the array of needle assembly storage compartments are coupled via a hinge.

2. The needle assembly storage device according to claim 1, wherein each needle assembly storage compartment within the array of needle assembly storage compartments comprises:
   a storage cavity having a first portion housing a needle hub and a second portion housing an injection needle coupled to the needle hub; and
   an opening.

3. The needle assembly storage device according to claim 2, wherein the second portion has a cross-sectional shape of one of a circle and a triangle.

4. The needle assembly storage device according to claim 1, wherein the array is shaped as one of a ring, an ellipsoid, and a helix.

5. The needle assembly storage device according to claim 1, wherein openings of the needle assembly storage compartments are sealed by at least one membrane.

6. The needle assembly storage device according to claim 1, wherein the housing comprises:
   a top wall;
   a bottom wall; and
   a side wall coupling the top wall to the bottom wall.

7. The needle assembly storage device according to claim 6, wherein the housing further comprises:
   a hinge connecting one of the top wall and the bottom wall to the side wall; and
   a connector for selectively locking the one of the top wall and the bottom wall to the side wall.

8. The needle assembly storage device according to claim 1, wherein the actuator includes a geared surface mating with a corresponding geared surface on the array.

9. The needle assembly storage device according to claim 1, wherein the actuation of the actuator moves the array a predetermined step distance (SD).

10. The needle assembly storage device according to claim 9, wherein the step distance (SD) is substantially equal to a width of one of the needle assembly storage compartments.

11. The needle assembly storage device according to claim 1, further comprising:
    a lock preventing the actuator from being actuated after a number of actuations equals a number of the needle assembly storage compartments in the array.

12. The needle assembly storage device according to claim 1, further comprising:
    an indicator disposed on the housing and displaying a number of unused needle assemblies in the array.

13. The needle assembly storage device according to claim 1, further comprising:
    a door disposed on the housing and adapted to selectively cover the opening.

14. The needle assembly storage device according to claim 13, wherein the door is movable between a closed position (C) covering the opening and an open position (O) in which the opening is uncovered, and wherein the door is biased in the closed position (C).

15. The needle assembly storage device according to claim 1, further comprising:
    a locking mechanism for preventing movement of at least one of the actuator and the array.

16. The needle assembly storage device according to claim 15, wherein the locking mechanism comprises:
    a notch formed on the actuator;

a door disposed on the housing and adapted to selectively cover the opening; and a protrusion formed on the door, wherein when the door is in the closed position (C), the protrusion engages the notch and prevents actuation of the actuator.

17. The needle assembly storage device according to claim 15, wherein the locking mechanism comprises:
   at least one recess formed on the array; and
   a latch arm disposed in the housing and moveable between a first position engaging the recess and a second position disengaging the recess, wherein when the latch arm is in the first position, movement of the array in one direction is prevented.

18. The needle assembly storage device according to claim 15, wherein the locking mechanism comprises:
   a cog wheel including a plurality of cogs;
   at least one projection formed on the actuator, wherein when the actuator moves in a first direction, the at least one projection is deflected by the cogs and wherein the at least one projection abuts one of the plurality of cogs preventing movement of the actuator in a second direction.

19. The needle assembly storage device according to claim 1, wherein the actuator is one of a dial wheel, a lever, a switch, and a button.

20. The needle assembly storage device according to claim 1, wherein a guide is formed around the opening to align the injection device with a needle assembly in a given one of the needle assembly storage compartments.

21. The needle assembly storage device according to claim 1, wherein the array is formed in a linear arrangement by injection-molding, filled with needle assemblies and subsequently formed into a ring shape.

* * * * *